(12) United States Patent
Buisine et al.

(10) Patent No.: US 11,613,465 B2
(45) Date of Patent: Mar. 28, 2023

(54) METHOD FOR PRODUCING A FLUORINE- AND SULFUR-BEARING COMPOUND AND SALTS THEREOF IN AN AQUEOUS MEDIUM

(71) Applicant: RHODIA OPERATIONS, Paris (FR)

(72) Inventors: Olivier Buisine, Saint Genis-Laval (FR); François Metz, Irigny (FR)

(73) Assignee: RHODIA OPERATIONS, Lyons (FR)

( * ) Notice: Subject to any disclaimer, the term of this patent is extended or adjusted under 35 U.S.C. 154(b) by 0 days.

(21) Appl. No.: 15/101,138

(22) PCT Filed: Dec. 3, 2014

(86) PCT No.: PCT/EP2014/076355
§ 371 (c)(1),
(2) Date: Jun. 2, 2016

(87) PCT Pub. No.: WO2015/082519
PCT Pub. Date: Jun. 11, 2015

(65) Prior Publication Data
US 2016/0304347 A1  Oct. 20, 2016

(30) Foreign Application Priority Data
Dec. 5, 2013 (FR) ..................... 1362136

(51) Int. Cl.
C01B 21/093 (2006.01)
C01B 21/086 (2006.01)
H01M 10/0568 (2010.01)
C07C 303/40 (2006.01)
H01M 10/052 (2010.01)

(52) U.S. Cl.
CPC .......... C01B 21/093 (2013.01); C01B 21/086 (2013.01); C01B 21/0935 (2013.01); C07C 303/40 (2013.01); H01M 10/052 (2013.01); H01M 10/0568 (2013.01); H01M 2300/0025 (2013.01)

(58) Field of Classification Search
CPC .. C01B 21/086; C01B 21/093; C01B 21/0935
See application file for complete search history.

(56) References Cited

U.S. PATENT DOCUMENTS

| | | | | |
|---|---|---|---|---|
| 8,722,005 | B1* | 5/2014 | Poshusta | C01B 21/0935 423/386 |
| 2004/0097757 | A1* | 5/2004 | Cernik | C01B 21/0935 562/818 |
| 2012/0009113 | A1* | 1/2012 | Honda | C01B 21/093 423/386 |
| 2012/0014859 | A1 | 1/2012 | Honda et al. | |
| 2012/0041233 | A1 | 2/2012 | Sato et al. | |
| 2013/0331609 | A1 | 12/2013 | Tsubokura et al. | |
| 2014/0241973 | A1 | 8/2014 | Fukunaga et al. | |
| 2016/0301106 | A1* | 10/2016 | Schmidt | C01B 21/086 |
| 2016/0308247 | A1* | 10/2016 | Buisine | C01B 21/0935 |

FOREIGN PATENT DOCUMENTS

| | | | |
|---|---|---|---|
| EP | 2 660 196 A1 | 11/2013 | |
| FR | WO 2012160280 A2 * | 11/2012 | ........... C01B 21/086 |
| JP | 2010-254543 A | 11/2010 | |
| JP | 2012-136429 A | 7/2012 | |
| JP | 2013-87019 A | 5/2013 | |

OTHER PUBLICATIONS

Martin Beran et al: "A New Method of the Preparation of Imido-bis(sulfuric acid) Dihalogenide, (F,Cl), and the Potassium Salt of Imido-bis(sulfuric acid) Difluoride", ZAAC (Journal for Inorganic and General Chemistry), vol. 631, No. 1, Jan. 1, 2005, pp. 55-59, Wiley-VCH.

Hong-Bo Han et al: "Lithium bis(fluorosulfonyl)imide (LiFSI) as conducting salt for nonaqueous liquid electrolytes for lithium-ion batteries: Physicochemical and electrochemical properties", Journal of Power Sources, Elsevier SA, CH, vol. 196, No. 7, Dec. 10, 2010, pp. 3623-3632.

William Davies et al: "CCLXXXVI.—Aromatic Sulphonyl Fluorides. A Convenient Method of Preparation", Journal of the Chemical Society (Resumed), No. 0, Jan. 1, 1931, pp. 2104-2109.

John K. Ruff and Max Lustig, "Imidodisulfuryl Fluoride, Cesium Imidodisulfuryl Fluoride and Fluoroimidodisulfuryl Fluoride", Inorganic Syntheses, 1968, vol. XI, p. 138-143.

Martin Beran and Jiri Prihoda, "A New Method of the Preparation of Imido-bis(sulfuric acid) Dihalogenide, (F,CI), and the Potassium Salt of Imido-bis(sulfuric acid) Difluoride", Z. Anorg. Allg. Chem. (2005), 631, pp. 55-59.

* cited by examiner

*Primary Examiner* — Ngoc-Yen Nguyen
(74) *Attorney, Agent, or Firm* — Osha Bergman Watanabe & Burton LLP

(57) ABSTRACT

The invention relates to a method for producing a fluorine- and sulphur-bearing compound of formula F—SO—R (I) or F—$SO_2$—R (II), comprising the reaction, in the presence of water, of at least one salt providing a fluoride anion and at least one halgoenosulfoxide compound of formula X—SO—R' (I0) from a halogenosulfonyl compound of formula X—$SO_2$—R' (II0), in which X is a halogen atom other than fluorine and R and R' are each a group linked by a covalent bond to the sulphur atom, said bond linking the sulphur atom with a nitrogen atom. The invention also relates to a method for producing salts of a fluorine- and sulphur-bearing compound of formula F—SO—R (I) or F—$SO_2$—R (II) which are advantageously used as electrolyte salts, as precursors of antistatic agents or as surfactant precursors.

5 Claims, No Drawings

METHOD FOR PRODUCING A FLUORINE- AND SULFUR-BEARING COMPOUND AND SALTS THEREOF IN AN AQUEOUS MEDIUM

This application is a U.S. national phase entry under 35 U.S.C. § 371 of International Application No. PCT/EP2014/076355, filed on Dec. 3, 2014, which claims priority to French Application No. 1362136, filed on Dec. 5, 2013. The entire contents of these applications are explicitly incorporated herein by this reference.

The present invention relates to the field of the preparation of fluorine-containing and sulfur-containing compounds in an aqueous medium and of the preparation of the salts of said compounds which are of use in applications such as electronics and electrochromism. More particularly, a subject of the present invention is the preparation of salts of bis(fluorosulfonyl)imide acid (HFSI), in particular lithium bis(fluorosulfonyl)imide (LiFSI).

The production of HFSI and of LiFSI is widely described in the literature. Among the various technologies described, the majority use a fluorination reaction either with HF or with metal fluorides. The use of metal fluorides is problematic since it is often not very efficient and uses expensive reagents such as fluorosulfuric acid. For example, fluorination with potassium fluoride in nitromethane or other polar organic solvents is not very efficient in terms of yield (WO 2002/053494). Other technologies have been developed, for example using chlorosulfonyl isocyanate in the presence of oleum and of ammonium fluoride (JP 2012-162470) or else using urea and fluorosulfonic acid, but these technologies suffer because of the strong corrosion of the medium and also the exothermicity of the reaction. These drawbacks make these technologies poorly suited to industrial production of bis(fluorosulfonyl)imide acid and of salts thereof.

Thus, there is a great need to produce bis(fluorosulfonyl) imide acid (HFSI) and more generally fluorine-containing and sulfur-containing compounds and the salts thereof according to an alternative process which remedies the drawbacks mentioned above.

Surprisingly, the applicant has developed a novel process for producing fluorine-containing and sulfur-containing compounds and salts thereof which operates under mild conditions and without exothermicity. The process according to the present invention has the advantage of being able to be easily carried out on an industrial scale. It carries out a fluorination reaction which is performed in an aqueous medium. The use of water as solvent makes it possible not only to improve the performance level of the fluorination reaction in comparison with those obtained by carrying out a fluorination reaction performed in an anhydrous medium, but also to easily separate the fluorine-containing and sulfur-containing compound formed, generally in salified form, from the fluorination medium.

A subject of the present invention is a process for preparing a fluorine-containing and sulfur-containing compound of formula F—SO—R (I) or F—SO$_2$—R (II) comprising the reaction, in the presence of water, of at least one salt providing a fluoride anion and of at least one halosulfoxide compound of formula X—SO—R' (I0), respectively of a halosulfonyl compound of formula X—SO$_2$—R' (II0), where X is a halogen atom other than fluorine and R and R' are each a group bonded via a covalent bond to the sulfur atom, said bond bonding said sulfur atom with a nitrogen atom.

Said halosulfoxide compound of formula (I0) or said halosulfonyl compound of formula (II0) used as reagent for carrying out the process according to the invention may be in acid form or in salified form, for example in the form of an alkali metal salt, an alkaline earth metal salt or an organic salt in ionic liquid form, in particular an onium salt and more particularly an ammonium, phosphonium, imidazolium, pyridinium or guanidinium salt.

The process of the invention performs a fluorination reaction or a halogen/fluorine exchange reaction, the halogen atom(s) other than fluorine being exchanged with fluorine. The reaction scheme of the process of the invention is given hereinafter in order to facilitate understanding without, however, binding the scope of the invention to said scheme.

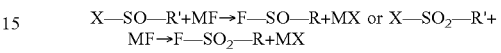

X—SO—R'+MF→F—SO—R+MX or X—SO$_2$—R'+ MF→F—SO$_2$—R+MX

In the equations above, M is the cation associated with the fluoride anion. The R and R' groups are identical when R' comprises no halogen atom other than fluorine capable of being affected by said fluorination reaction according to the process of the invention. R and R' are different and differ from one another by the nature of the halogen when R' comprises one or more halogen atoms, other than fluorine, affected by said fluorination reaction.

More preferably, the object of the process of the invention is to prepare said fluorine-containing and sulfur-containing compound of formula F—SO$_2$—R (II) from said halosulfonyl compound of formula X—SO$_2$—R' (II0).

In the process according to the invention, R and R' are each a group bonded via a covalent bond to the sulfur atom, said bond bonding said sulfur atom with a nitrogen atom. According to one preferred embodiment, said nitrogen atom is bonded to another —SO$_2$— or —SO— group. Thus, R and R' can be selected such that the compounds (I) and (II) comprise a nitrogen atom bonded to two —SO$_2$— or —SO— groups.

The R group may be selected from the group consisting of:
- an —NHSO$_2$F group,
- an —NHSOF group,
- an —NM'SO$_2$F group,
- an —NM'SOF group,
- an —NR$_1$R$_{10}$ group,
- an —NHSO$_2$R$_1$ group,
- an —NHSOR$_1$ group, and
- an —NHCOR$_1$ group, where M' is an alkali or alkaline-earth metal or an onium ion, and where R$_1$ and R$_{10}$, which may be identical or different, are selected from the group consisting of a hydrogen atom, a saturated or unsaturated, linear, branched or cyclic hydrocarbon-based chain having from 1 to 15 carbon atoms, a fluoroalkyl, perfluoroalkyl or fluoroalkenyl chain having from 1 to 15 carbon atoms, and an aromatic group.

According to one preferred embodiment of the process of the invention, the R group is selected from the group consisting of an —NHSO$_2$F group, an —NM'SO$_2$F group (M' being an alkali or alkaline-earth metal), an group, an —NR$_1$R$_{10}$ group, an —NHSO$_2$R$_1$ group and an —NHCOR$_1$ group; where R$_1$ and R$_{10}$, which may be identical or different, are selected from the group consisting of a hydrogen atom, a saturated or unsaturated, linear, branched or cyclic hydrocarbon-based chain having from 1 to 15 carbon atoms, a fluoroalkyl, perfluoroalkyl or fluoroalkenyl chain having from 1 to 15 carbon atoms, and an aromatic group.

The aromatic group covers in particular a monocyclic or polycyclic aryl or heteroaryl radical, the aryl radical preferably being a 5- to 6-membered aromatic ring. Said aryl or heteroaryl radical can itself bear one or more substituent(s), for example a saturated or unsaturated, linear or branched carbon-based chain, or a halogen, hydroxyl, trifluoromethyl, trifluoromethoxy, methoxy, carboxy, amino, oxo, nitro or cyano group.

Very advantageously, the R group is an —$NHSO_2F$ group, an —$NM'SO_2F$ group(M' being an alkali or alkaline-earth metal) or an —$NHSO_2R_1$ group, where $R_1$ is a fluoroalkyl or perfluoroalkyl chain, preferentially a perfluoroalkyl chain having from 1 to 5 carbon atoms, very preferentially $R_1$ is the —$CF_3$ group.

According to this embodiment, the R' group is selected from the group consisting of an —$NHSO_2X$ group (X having the definition given above), an —$NR'_1R'_{10}$ group, an —$NHSO_2R'_1$ group and an —$NHCOR'_1$ group; where $R'_1$ and $R'_{10}$, which may be identical or different, are selected from the group consisting of a hydrogen atom, a saturated or unsaturated, linear, branched or cyclic hydrocarbon-based chain having from 1 to 15 carbon atoms, a haloalkyl, perhaloalkyl or haloalkenyl chain in which the halogen atom(s) is (are) selected from bromine, chlorine, fluorine and iodine and which has from 1 to 15 carbon atoms, and an aromatic group. Very advantageously, the R' group is an —$NHSO_2X$ group (X having the definition given above, preferentially X is chlorine) or an —$NHSO_2R'_1$ group where $R'_1$ is a haloalkyl or perhaloalkyl chain.

Said embodiment is particularly advantageous when the fluorination reaction is carried out in the presence of said halosulfonyl compound of formula X—$SO_2$—R' (II0) in order to prepare said fluorine-containing and sulfur-containing compound of formula F—$SO_2$—R (II).

Very preferably, the process of the invention is carried out using a halosulfonyl compound of formula (II0) X—$SO_2$—NH—$SO_2$—X (X having the definition given above, preferentially X is chlorine) so as to prepare the compound F—$SO_2$—NH—$SO_2$—F (II), called bis(fluorosulfonyl)imide acid (HFSI) or a salt of said compound (F—$SO_2$—NK—$SO_2$—F where M' is an alkali or alkaline-earth metal). A metal salt or an organic salt of said halosulfonyl compound of formula (II0) can also be used. Likewise very preferably, the process of the invention is carried out using a halosulfonyl compound of formula (II0) X—$SO_2$—NH—$SO_2$—$CF_3$ (X having the definition given above, preferentially X is chlorine) so as to prepare the compound F—$SO_2$—NH—$SO_2$—$CF_3$ (II).

Moreover, an embodiment is also described herein in which the R group is an alkyl hydrocarbon-based chain, a fluoroalkyl, perfluoroalkyl or fluoroalkenyl chain, an aromatic group, an alkenyl group or a nitrile group. Said alkyl chains and said aromatic and alkenyl groups can be substituted. The term "alkyl" covers in particular a saturated and linear, branched or cyclic carbon-based chain which may contain one or more heteroatoms (N, O, S), which may contain one or more unsaturations, and which may contain one or more substituents, unless otherwise indicated. Preferably, such a linear or branched chain comprises from 1 to 15 carbon atoms, and preferably from 1 or 2 to 10 carbon atoms. The term "aromatic" covers in particular a monocyclic or polycyclic aryl or heteroaryl radical comprising carbon and hydrogen atoms. The aryl or heteroaryl radical is preferably a 5- to 6-membered aromatic ring comprising, for example, 1, 2, 3, 4 or 5 heteroatoms selected in particular from nitrogen, sulfur and oxygen. The aryl or heteroaryl radicals may themselves bear one or more substituents, for example, selected from the halogen, hydroxyl, trifluoromethyl, trifluoromethoxy, methoxy, carboxy, amino, oxo, nitro or cyano group. Examples of aromatic groups include, without being limited thereto, phenyl, tolyl, anthracenyl, fluorenyl, indenyl, azulenyl and naphthyl, and benzo-fused carbocyclic radicals such as 5,6,7,8-tetrahydronaphthyl. An aromatic group may be substituted with one or more substituents or unsubstituted. According to one variant, the aromatic ring is a monocyclic nucleus with 6 carbon atoms. The alkenyl group is typically a hydrocarbon-based group comprising an unsaturation (C=C) in the alpha position with respect to the sulfur atom of formula (I) or of formula (II).

However, the reactivity of the halosulfoxide and halosulfonyl compounds can vary according to the electron-richness of the R' group. Thus, the hydrolysis of the compounds in which R' is an aromatic group is relatively slow. Conversely, the reagents in which the X—SO— or X—$SO_2$— group is bonded to a nitrogen atom, in particular the compounds in which said nitrogen atom is bonded to another —$SO_2$— or —SO— group, are known to react violently with water.

In accordance with the process according to the invention, the nature of said salt providing at least said fluoride anion may be of varied nature. Advantageously, said salt is selected from metal fluorides, onium fluorides and mixtures thereof.

Said metal fluorides, advantageously used as salts providing fluoride anions in the process according to the invention, are preferentially fluorides in which the metal cations belong to groups IA, IIA and IIB of the periodic table of elements. By way of examples of cations which are suitable for carrying out the process of the invention, mention may more particularly be made, among the cations of group IA, of lithium, sodium, potassium and cesium cations, among the cations of group IIA, of magnesium and calcium cations, and among the cations of group IIB, of the zinc cation. Among the abovementioned salts, potassium fluoride and sodium fluoride are preferably selected.

The invention does not exclude the use of double salts such as double aluminum and sodium or potassium fluorides and sodium or potassium fluosilicates.

Said onium fluorides, advantageously used as salts providing fluoride anions in the process according to the invention, are preferentially selected from ammonium fluorides, phosphonium fluorides, imidazolium fluorides, guanidinium fluorides and pyridinium fluorides, taken alone or as a mixture.

The ammonium fluorides and the phosphonium fluorides are salts of which the cation corresponds in particular to the following formula (III):

(III)

wherein:
W represents N or P,
$R_2$, $R_3$, $R_4$ and $R_5$, which may be identical or different, represent:
 a linear or branched alkyl group having 1 to 16 carbon atoms and optionally substituted with one or more heteroatoms or phenyl, hydroxyl, halogen, nitro, alkoxy or alkoxycarbonyl groups, the alkoxy groups having 1 to 4 carbon atoms;
 a linear or branched alkenyl group having 2 to 12 carbon atoms;

an aryl group having 6 to 10 carbon atoms, optionally substituted with one or more heteroatoms or alkyl groups having 1 to 4 carbon atoms, alkoxy groups, alkoxycarbonyl groups, the alkoxy group having 1 to 4 carbon atoms, or halogen groups.

The ammonium fluorides and the phosphonium fluorides, preferentially used for implementing the process according to the invention, have a cation which corresponds to the formula (III) in which W is a nitrogen or phosphorus atom and $R_2$, $R_3$, $R_4$ and $R_5$, which may be identical or different, are selected from a linear or branched alkyl group having 1 to 4 carbon atoms, and a benzyl group. By way of more specific examples, mention may be made of tetrabutylammonium fluoride, methyltri(n-butyl)ammonium fluoride, N-methyl-N,N,N-trioctylammonium fluoride, trimethylphenylphosphonium fluoride, tetrabutylphosphonium fluoride, methyltri(n-butyl)phosphonium fluoride, methyltri(isobutyl) phosphonium fluoride and diisobutyl-n-octylmethylphosphonium fluoride. Tetrabutylammonium fluoride ($R_2$=$R_3$=$R_4$=$R_5$=butyl and W=N) and tetrabutylphosphonium fluoride ($R_2$=$R_3$=$R_4$=$R_5$=butyl and W=P) are preferentially selected.

The imidazolium fluorides and the pyridinium fluorides are salts providing fluoride anions and the cation of which corresponds, respectively, to formula (IV) or formula (V) below:

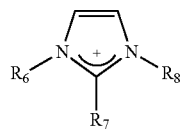

(IV)

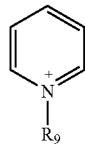

(V)

in which:
- the $R_6$ group represents an alkyl group having from 1 to 20 carbon atoms,
- the $R_7$ group represents a hydrogen atom or an alkyl group having from 1 to 4 carbon atoms,
- the $R_8$ group represents an alkyl group having from 1 to 4 carbon atoms,
- the $R_9$ group represents an alkyl group having from 1 to 6 carbon atoms.

Among the cations corresponding to formulae (IV) and (V), 1-alkyl-2,3-dimethylimidazolium ($R_6$=$C_1$-$C_{20}$ alkyl, $R_7$=$R_8$=methyl), 1-alkyl-3-methylimidazolium ($R_6$=$C_1$-$C_{20}$ alkyl, $R_7$=H, $R_8$=methyl) and 1-alkylpyridinium ($R_9$=$C_1$-$C_6$ alkyl) cations are preferred. As more specific examples of imidazolium fluorides, mention may be made of 1-alkyl-2,3-dimethylimidazolium fluorides, such as 1-ethyl-2,3-dimethylimidazolium fluoride, 1-butyl-2,3-dimethylimidazolium fluoride or 1-hexyl-2,3-dimethylimidazolium fluoride; 1-butyl-2,3-dimethylimidazolium tetrafluoroborate, 1-hexyl-2,3-dimethylimidazolium tetrafluoroborate; 1-alkyl-3-methylimidazolium fluorides, such as 1-ethyl-3-methylimidazolium fluoride, 1-hexyl-3-methylimidazolium fluoride, 1-octyl-3-methylimidazolium fluoride, 1-decyl-3-methylimidazolium fluoride, 1-dodecyl-3-methylimidazolium fluoride, 1-tetradécyl-3-methylimidazolium fluoride, 1-hexadecyl-3-méthylimidazolium fluoride or 1-octadecyl-3-methylimidazolium fluoride; 1-butyl-3-methylimidazolium hexafluorophosphate, 1-hexyl-3-methylimidazolium hexafluorophosphate, 1-octyl-3-methylimidazolium hexafluorophosphate; 1-butyl-3-methylimidazolium tetrafluoroborate, 1-hexyl-3-methylimidazolium tetrafluoroborate. The preferred imidazolium fluorides are 1-butyl-3-methylimidazolium hexafluorophosphate and 1-butyl-3-methylimidazolium tetrafluoroborate. As more specific examples of pyridinium fluorides, mention may be made of 1-alkylpyridinium salts, such as 1-ethylpyridinium fluoride, 1-butylpyridinium fluoride, 1-hexylpyridinium fluoride; 1-butylpyridinium hexafluorophosphate, 1-hexylpyridinium hexafluorophosphate; 1-butylpyridinium tetrafluoroborate, 1-hexylpyridinium tetrafluoroborate.

Said halosulfoxide compound of formula (I0) or said halosulfonyl compound of formula (II0) used as reagent for carrying out the process according to the invention is in acid form or in salified form. In salified form, use is advantageously made of alkali and alkaline-earth metal salts or else organic salts in ionic liquid form, in particular onium salts and more particularly ammonium salts (very preferentially a tetrabutylammonium salt), phosphonium salts, imidazolium salts, pyridinium salts and guanidinium salts.

In accordance with the process of the invention, the fluorination reaction between said compound of formula (I0) or said compound of formula (II0) and the salt providing the fluoride anion is performed in the presence of water. The amount of said salt in the water is such that it represents from 1% by weight, preferably from 10% by weight, up to saturation of the water at the reaction temperature. The reaction can also be carried out in an aqueous-organic medium, in particular using a polar or nonpolar organic solvent. The fluorination reaction is advantageously carried out at a temperature between 20 and 160° C., preferably between 60 and 120° C. It is advantageously carried out under atmospheric pressure. It is carried out for a period preferentially of between a few minutes and 20 hours, very preferentially between 0.5 and 10 hours.

According to the process of the invention, the mole ratio between the number of moles of said halosulfoxide compound or said halosulfonyl compound and the number of moles of salt, expressed as fluoride anion, is between 1 and 20 and preferably between 3 and 10.

In accordance with the process of the invention, the fluorination reaction is carried out in a single-phase or liquid/liquid two-phase medium.

The process of the invention is simple to carry out. The reagents can be introduced in any order according to different variants, but some are preferred. One preferred embodiment consists in introducing said compound of formula (I0) or (II0) onto a mixture formed from water and from said salt providing at least said fluoride anion. The addition of said compound of formula (I0) or (II0) is preferentially carried out once said aqueous mixture has been heated to a temperature included in the abovementioned range.

The fluorine-containing and sulfur-containing compound of formula (I) or (II), obtained at the end of carrying out said fluorination reaction, is in the form of a neutral molecule or else in salified form. The salified form is obtained when said halosulfoxide compound or said halosulfonyl compound has an acidic hydrogen, the pKa of which in water is less than 7. Preferably, said fluorine-containing and sulfur-containing compound of formula (I) or (II) is obtained in salified form. For example, in the implementation of the preferred embodiment of the process according to the invention consisting in using bis(chlorosulfonyl)imide acid or a salt thereof as compound of formula (II0), a salt of bis(fluorosulfonyl) imide acid, for example a potassium salt (potassium bis (fluorosulfonyl)imide), is obtained at the end of carrying out said fluorination reaction, when said salt providing said fluoride anion is potassium fluoride The process for preparing said fluorine-containing and sulfur-containing compound according to the invention is advantageously carried out in equipment capable of withstanding the corrosion of the reaction medium.

For this purpose, materials are selected for the part in contact with the reaction medium that are corrosion-resistant, such as the alloys based on molybdenum, chromium, cobalt, iron, copper, manganese, titanium, zirconium, aluminum, carbon and tungsten, sold under the Hastelloy® brands or the alloys of nickel, chromium, iron and manganese to which copper and/or molybdenum are added, sold under the name Inconel® or Monel™, and more particularly the Hastelloy C 276 or Inconel 600, 625 or 718 alloys. Stainless steels may also be selected, such as austenitic steels [Robert H. Perry et al., *Perry's Chemical Engineers' Handbook, Sixth Edition* (1984), pages 23-44] and more particularly the 304, 304 L, 316 or 316 L stainless steels. A steel having a nickel content of at most 22% by weight, preferably of between 6% and 20% and more preferentially of between 8% and 14%, is used. The 304 and 304 L steels have a nickel content that varies between 8% and 12%, and the 316 and 316 L steels have a nickel content that varies between 10% and 14%. More particularly, 316 L steels are selected.

Use may also be made of equipment consisting of or coated with a polymeric compound resistant to the corrosion of the reaction medium. Mention may in particular be made of materials such as PTFE (polytetrafluoroethylene or Teflon) or PFA (perfluoroalkyl resins). It will not be outside the scope of the invention to use an equivalent material.

As other materials capable of being suitable for being in contact with the reaction medium, mention may also be made of graphite derivatives.

When the fluorine-containing and sulfur-containing compound of formula (I) or (II), obtained at the end of carrying out said fluorination reaction, is immiscible in the reaction medium, in particular when it is a neutral molecule or a salt of said compound immiscible in the reaction medium, for example an onium salt, said compound is isolated, purified, and optionally converted according to conventional techniques known to those skilled in the art.

A subject of the present invention is also a process for preparing at least one salt of said fluorine-containing and sulfur-containing compound of formula (I) or (II) using the process for preparing said compound of formula (I) or (II) as described above. Said salt of said fluorine-containing and sulfur-containing compound of formula (I) or (II) is preferentially a salt of an alkali metal (Li, Na, K, Rb, Cs), a salt of an alkaline-earth metal, a salt of a transition metal or a salt selected from lanthanides. Preferably, it is a salt of an alkali metal, very preferentially a lithium salt. In particular, when said fluorine-containing and sulfur-containing compound of formula (I) or (II) is a salt of bis(fluorosulfonyl)imide acid, lithium bis(fluorosulfonyl)imide (LiFSI) is advantageously prepared. The process for preparing at least said salt of said fluorine-containing and sulfur-containing compound of formula (I) or (II) according to the invention comprises the preparation of said compound of formula (I) or (II) in salified form according to the process described above, followed by a step of liquid/liquid extraction, and then the implementation either of a sequence comprising the steps of acidification, of recovery of the acid obtained and of neutralization, or of a cation exchange reaction.

The process for preparing at least said salt of said fluorine-containing and sulfur-containing compound of formula (I) or (II) according to the invention is adapted when said compound of formula (I) or (II), obtained at the end of said fluorination reaction, is in the form of a salt that is miscible in the aqueous reaction medium. Said reaction medium is subjected to a liquid/liquid extraction step so as to extract said salt of said compound of formula (I) or (II) obtained at the end of said fluorination reaction. More specifically, said reaction medium is brought into contact with an onium salt resulting in the formation of an organic phase comprising the complex resulting from the reaction of said miscible salt of said compound of formula (I) or (II), obtained at the end of said fluorination reaction, with the onium salt, and an aqueous phase comprising the various salts, in particular that resulting from the reaction of the cation of said miscible salt with the onium anion.

Said onium salt advantageously used for carrying out the liquid/liquid extraction is preferentially selected from ammonium salts, phosphonium salts, imidazolium salts, guanidinium salts and pyridinium salts, taken alone or as a mixture. The formulae of these salts were specified above in the present description.

Said liquid/liquid extraction step is carried out in the presence of an organic solvent, preferentially a halogenated organic solvent, for example dichloromethane or dichloroethane. It is carried out at a temperature between 10 and 100° C., preferentially between 20 and 40° C. Said liquid/liquid extraction step has already been described in patent application FR 2 933 693.

Said complex obtained is present in the organic phase and the aqueous and organic phases are separated, in particular by settling out, so as to recover an ionic liquid of said compound of formula (I) or (II).

According to a first embodiment of the process for preparing said salt of said fluorine-containing and sulfur-containing compound of formula (I) or (II) according to the invention, said complex obtained in said organic phase is acidified so as to free therefrom the acid function. Said acidification step is carried out by means of a treatment with a strong Brönstedt acid, for example sulfuric acid, hydrochloric acid, phosphoric acid, sulfonic acid or nitric acid. The stoichiometry of protons provided by the acid with respect to said complex ranges from 1 to 10 molar equivalents, preferably from 1 to 4 molar equivalents. The acidification is preferentially carried out at a temperature between 10° C. and 50° C. At the end of said acidification step, said compound of formula (I) or (II) is in acid form in the organic phase. It is recovered according to conventional techniques known to those skilled in the art, in particular by distillation or by extraction. Said compound of formula (I) or (II) in acid form is very preferentially recovered by distillation. The organic solvent used for carrying out the liquid/liquid extraction step, prior to the settling out step, is first distilled at atmospheric pressure, and then said compound of formula (I) or (II) in acid form is distilled under reduced pressure. The carrying out of said distillation step is advantageous since it makes it possible to achieve said compound with the high purity required for electronic applications. Said compound of formula (I) or (II) in acid form thus obtained in purified form is dissolved in an organic solvent so as to be subjected to a neutralization step. Said organic solvent is preferentially a chlorinated aliphatic solvent or an aromatic solvent. In particular, it is dichloromethane or dichloroethane. The neutralization is carried out by treatment with a metal hydroxide, a metal chloride or a metal hydride, the metal cation associated with the hydroxide anion being a monovalent or divalent cation, preferably the lithium cation. Preferably, the neutralization is carried out in the presence of lithium hydroxide or lithium chloride. The neutralization is carried out at a temperature between 10 and 100° C., preferably between 10 and 40° C. Said neutralization step is easy to carry out. Advantageously, said compound of formula (I) or (II) in acid form, obtained after distillation, is dissolved in an organic solvent and then an aqueous solution of metal hydroxide, chloride or hydride is added. The organic and aqueous phases are separated by settling out or filtration and the organic phase is evaporated off. The salt of said fluorine-containing and sulfur-containing compound of formula (I) or (II) is advantageously recovered from the aqueous phase.

According to a second embodiment of the process for preparing said salt of said fluorine-containing and sulfur-containing compound of formula (I) or (II) according to the invention, a cation exchange reaction is carried out on the complex obtained after said settling out step explained above in the present description. Said cation exchange reaction is carried out by bringing the organic phase comprising said complex into contact with an aqueous solution of metal hydroxide or of metal halide, the metal cation associated with the hydroxide or halide anion being monovalent or divalent. Preferably, said metal hydroxide is lithium hydroxide. The stoichiometry of metal cation with respect to said complex is between 0.5 and 5 molar equivalents, preferably between 1 and 2. Said exchange reaction is carried out at a temperature between 10 and 100° C., preferably between 10 and 40° C. At the end of the reaction, the organic and aqueous phases are separated by settling out. The organic phase is evaporated off and said salt of said fluorine-containing and sulfur-containing compound of formula (I) or (II), obtained from the aqueous phase, is preferentially dried under vacuum.

Another subject of the present invention is the use of said fluorine-containing and sulfur-containing compound of formula F—SO—R (I) or F—SO$_2$—R (II) or of a salt of said fluorine-containing and sulfur-containing compound of formula (I) or (II), prepared according to the processes described above, as electrolyte salts, as antistatic agent precursors or else as surfactant precursors. In particular, said compound of formula (I) or (II) or the salts thereof are advantageously used as electrolytes for the manufacture of batteries, in the electrochromism and electronics field. They are advantageously used as antistatic agents for the manufacture of pressure-sensitive adhesives (PSAs). As antistatic agents, they may also be used as components of lubricants. They are used in optical materials such as electroluminescent devices and are incorporated into the composition of photovoltaic panels.

Exemplary embodiments of the invention are given hereinafter. These examples are given by way of nonlimiting illustration.

EXAMPLES 1 to 5

A solution of potassium fluoride in aqueous solution is brought to the reaction temperature in a glass reactor. Bis(chlorosulfonyl)imide, denoted HCSI, (10 grams, 47 mmol) is added over the course of 30 seconds and stirring is maintained for 2 hours at the reaction temperature. The reaction medium is diluted in water for the analysis carried out by $^{19}$F NMR in order to calculate the yield of potassium bis(fluorosulfonyl)imide (KFSI).

The following table collates the operating conditions used and the results obtained:

| Example No. | KF stoichiometry (equivalents) | H$_2$O/KF mole ratio | Temperature (° C.) | HCSI conversion (%) | KFSI yield (%) |
|---|---|---|---|---|---|
| 1 | 10 | 2.8 | 100 | 100% | 38% |
| 2 | 10 | 2.7 | 75 | 100% | 51% |
| 3 | 10 | 2.3 | 50 | 100% | 65% |
| 4 | 15 | 2.4 | 50 | 100% | 60% |
| 5 | 20.8 | 2.5 | 50 | 100% | 65% |

EXAMPLE 6 (comparative)

Fluorination with Zinc Fluoride in an Organic Medium

Zinc fluoride (5.1 g; 49 mmol) is dissolved in 90 grams of valeronitrile. Bis(chlorosulfonyl)imide is then added and stirring is maintained for 24 hours at ambient temperature.

An NMR analysis shows a 100% conversion of the bis(chlorosulfonyl)imide, and the yield of bis(fluorosulfonyl)imide zinc salt is 12%.

EXAMPLE 7

A solution of potassium fluoride (27 g, 0.46 mol) in aqueous solution (23 g of water) is brought to the temperature of 100° C. in a glass reactor. The potassium bis(chlorosulfonyl)imide, denoted KCSI, (11.8 grams, 46 mmol) is added over the course of 30 seconds and stirring is maintained for 2 hours at this reaction temperature. The reaction medium is diluted in water and brought back to ambient temperature. The $^{19}$F NMR analysis indicates that the potassium bis(fluorosulfonyl)imide (KFSI) yield obtained is 69%.

EXAMPLE 8

N,N,N-tri-n-octyl-N-methylammonium bis(chlorosulfonyl)imide (27 g; 46 mmol) is added to a solution of potassium fluoride (27 g, 0.46 mol) in water (23 g) brought to a temperature of 120° C. The medium is left to stir for two hours. After a return to ambient temperature, the $^{19}$F NMR analysis indicates that the N,N,N-tri-n-octyl-N-methylammonium bis(fluorosulfonyl)imide yield is 49%.

EXAMPLE 9

Potassium bis(chlorosulfonyl)imide (10 g; 46 mmol) is added to a solution of potassium fluoride (27 g, 0.46 mol) in water (23 g) brought to a temperature of 120° C. The medium is left to stir for 30 minutes. After a return to ambient temperature, the $^{19}$F NMR analysis indicates that the potassium bis(fluorosulfonyl)imide yield is 76%.

The invention claimed is:
1. A process for preparing a fluorine-containing and sulfur-containing compound of formula F—SO$_2$—R (II), the process comprising the reaction, in the presence of water, of at least one salt providing a fluoride anion, wherein the salt providing a fluoride anion is potassium fluoride, and of a halosulfonyl compound of formula X—SO$_2$—R' (II0), where X is chlorine, R is an —NM'SO$_2$F group, M' being potassium, and R' is an —NHSO$_2$X group; wherein the H$_2$O/KF mole ratio is from 2.3 to 2.8, the molar equivalent of KF is from 10 to 20.8, the reaction temperature is 50° C. to 100° C., and the reaction time is between 0.5 hr and under 10 hr.

2. The process as defined in claim 1, further comprising: a step of liquid/liquid extraction, and then the implementation of a sequence comprising the steps of acidification, of recovery of the acid obtained and of neutralization.

3. The process as claimed in claim 1, further comprising: a step of liquid/liquid extraction, and then the implementation of a cation exchange reaction.

4. The process for preparing at least one salt of a fluorine-containing and sulfur-containing compound of formula (II) as claimed in claim 2, wherein said salt of said fluorine-containing and sulfur-containing compound of formula (II) is a salt of potassium.

5. The process for preparing at least one salt of a fluorine-containing and sulfur-containing compound of formula (II) as claimed in claim 3, wherein said salt of said fluorine-containing and sulfur-containing compound of formula (II) is a salt of potassium.

* * * * *